United States Patent
Barradeau et al.

(10) Patent No.: US 7,364,887 B2
(45) Date of Patent: Apr. 29, 2008

(54) USE OF PAK INHIBITOR FOR THE TREATMENT OF A JOINT DISEASE

(75) Inventors: Sebastian Barradeau, Paris (FR); Eckart Bartnik, Wiesbaden (DE); Joerg Czech, Marburg (DE); Andreas R. Klatt, Köln (DE); Ekkehard Leberer, Germering (DE); Thomas Leeuw, Greifenberg (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 282 days.

(21) Appl. No.: 10/893,025

(22) Filed: Jul. 16, 2004

(65) Prior Publication Data
US 2005/0037965 A1 Feb. 17, 2005

Related U.S. Application Data

(60) Provisional application No. 60/527,819, filed on Dec. 8, 2003.

(30) Foreign Application Priority Data
Jul. 18, 2003 (EP) ................... 03016303

(51) Int. Cl.
*A61K 38/00* (2006.01)
*G01N 33/68* (2006.01)
*A61P 19/02* (2006.01)

(52) U.S. Cl. .................... 435/183; 514/14; 514/44; 514/2; 435/194; 435/94.5

(58) Field of Classification Search ............... 435/183, 435/194, 94.5; 514/2, 12, 44
See application file for complete search history.

(56) References Cited

U.S. PATENT DOCUMENTS

| 5,698,445 A | 12/1997 | Abo et al. |
| 6,013,464 A * | 1/2000 | Abo et al. ............ 435/15 |
| 6,383,734 B1 | 5/2002 | Marshall et al. |

FOREIGN PATENT DOCUMENTS

WO     WO 00/60062     10/2000

OTHER PUBLICATIONS

Zhao et al (A Conserved Negative Regulatory region in alpha-PAK: Inhibition of PAK Kinase Reveals Their Morphological Roles Downstream of Cdc42 and Rac1. American Society of Microbiology. 1998. p. 2153-2163.*
Nheu et al The K252A Derivatives, inhibitors for the PAK/MLK kinase family, selectively block the growth of HAS transformants. The Cancer Journal Jul./Aug. 2002, vol. 8 Issue 4, p. 328-336.*

* cited by examiner

*Primary Examiner*—Nashaat T. Nashed
*Assistant Examiner*—Kagnew Gebreyesus

(57) ABSTRACT

The invention refers to the use of a p21-activated kinase (PAK) inhibitor for the treatment of a joint disease such as osteoarthritis or rheumatoid arthritis or for the treatment of a joint pain and the use of PAK as a target protein for the discovery of a PAK inhibitor as a medicament for the treatment of a joint disease.

5 Claims, 4 Drawing Sheets

USE OF PAK INHIBITOR FOR THE TREATMENT OF A JOINT DISEASE

FIELD OF THE INVENTION

The present invention refers to the use of a p21-activated kinase (PAK) inhibitor for the treatment of a joint disease such as osteoarthritis or rheumatoid arthritis or for the treatment of a joint pain and the use of PAK as a target protein for the discovery of a PAK inhibitor as a medicament for the treatment of a joint disease.

BACKGROUND OF THE INVENTION

Osteoarthritis is the most common disabling condition of man in the western world. Due to the aging of the population we have to face an ever-increasing population of patients, whose quality of life is severely affected. In addition, the disease carries a tremendous socio-economic burden with high direct and indirect costs. The current treatment modalities concentrate on the management of the pain associated with osteoarthritis, but we are still completely lacking any pharmacological treatment modalities able to slow, stop or even reverse the course of the disease.

Osteoarthritis can be viewed as the clinical and pathological outcome of a range of disorders that results in structural and functional failure of synovial joints. Osteoarthritis occurs when the dynamic equilibrium between the breakdown and repair of joint tissues is overwhelmed. Structural failure of articular cartilage can result from abnormal mechanical strains injuring healthy cartilage, as well as from failure of pathologically impaired cartilage degenerating under the influence of physiological mechanical strains. Morphological changes observed in osteoarthritis include cartilage erosion as well as a variable degree of synovial inflammation. These changes are attributed to a complex network of biochemical factors, including proteolytic enzymes, that lead to a breakdown of the cartilage macromolecules. Cytokines such as IL-1 and TNFα which are produced by activated synoviocytes, mononuclear cells or by articular cartilage itself, significantly upregulate metalloproteinases (MMP) and cytokine gene expression, and blunt compensatory synthesis pathways. For example, activation of the AP1-transcription factor complex by IL-1 and/or TNFα through signal transmission via MAPK (mitogene activated protein kinase)-pathways plays an important role for the regulation of expression of marker genes that are relevant for osteoarthritis.

A further biochemical factor involved in cartilage catabolism and genesis of inflammatory pain is PGE2 (prostaglandin E2). PGE2, an eicosanoid synthesized by cycloxygenase (COX)-1 and -2, is involved in IL-1-mediated proteoglycan degradation, and administration of PGE2 into conscious rats or mice induces hyperalgesia. Endogenous expression of IL-1β leads to induction of COX-2 in the human osteoarthritis joint.

Consequently, osteoarthritis is characterized by a slow progressive degeneration of articular cartilage. The exact etiology of osteoarthritis is not yet known, but the degradation of cartilage matrix components is generally agreed to be due to an increased synthesis and activation of extracellular proteinases, mainly matrix metalloproteinases, and cytokines that amplify degenerative processes. Novel approaches to treat osteoarthritis are required, and progress in understanding the biology of cartilage disorders has led to the use of genes whose products stimulate cartilage repair or inhibit breakdown of the cartilaginous matrix. Several studies illustrate e.g. the potential importance of modulating IL-1 activity as a means to reduce the progression of the structural changes in osteoarthritis.

Therefore, an object of the present invention is to find new therapeutic ways for the avoidance or reduction of the effects of the cartilage harming factors.

SUMMARY OF THE INVENTION

Surprisingly, PAK, in particular PAK1 has been identified as an important mediator of the IL-1 induced activation of signalling pathways leading to an upregulation of the expression of marker genes that are relevant for osteoarthritis.

PAK1 belongs to a member of the evolutionarily conserved family of serine/threonine kinases that are important for a variety of cellular functions including cell morphogenesis, motility, survival, mitosis, and angiogenesis. PAK's belong to the larger family of Ste20 protein kinases. Ste20p is a putative yeast mitogen-activated protein kinase kinase kinase kinase (MAP4K) involved in the mating pathway in *S. cerevisiae*. Its homologs in mammals, *Drosophila, Caenorhabditis* elegans and other organisms make up a large emerging group of protein kinases including members in human. The Ste20 group kinases are further divided into the p21-activated kinase (PAK) and germinal center kinase (GCK) families. They are characterized by the presence of a conserved kinase domain and a noncatalytic region of great structural diversity that enables the kinases to interact with various signalling molecules and regulatory proteins of the cytoskeleton.

Several publications have described a role for PAK's in the regulation of MAPK activity in mammalian cells (see e.g. Dan, C. et al. (2002) Mol. Cell Biol., 22, 567-577). MAPK cascades are crucial in a wide range of cellular events, transmitting signals from extracellular stimuli such as growth factors, cytokines and environmental stresses to activate transcription factors, resulting in regulation of gene expression (Johnson, G. L. and Lapadat, R. (2002) Science, 298, 1911-1912). Signalling is mediated by linear sequential phosphorylation of a triple-kinase module consisting of MAP kinase kinase kinase (MAP3K), MAP kinase kinase (MAP2K) and MAPK. The triple-kinase module and its activation mechanism are highly conserved in the eukaryotic evolution from yeast to mammals.

In mammalian cells PAKs are identified as downstream effector target of Cdc42 and Rac1, and binding of GTPases to Pak1 stimulates its kinase activity via autophosphorylation. PAKs form complexes specifically with activated (GTP-bound) p21, inhibiting p21 GTPase activity and leading to kinase autophosphorylation and activation. PAK family kinases, conserved from yeasts to humans, are directly activated by Cdc42 or Rac1 through interaction with a conserved N-terminal motif (corresponding to residues 71 to 137 in aPAK). Autophosphorylated kinase has a decreased affinity for Cdc42/Rac1, freeing the p21 for further stimulatory activities or downregulation by GTPase-activating proteins (Manser, E. et al. (1994) Nature, 367, 40-46). In addition to Rac1 and Cdc42, newly identified homologs of the Rho family of GTPases such as Wrch-1 and Chp can also activate PAKs and induce filopodium formation and stress fiber dissolution (Aronheim, A. et al. (1998) Curr. Biol. 8, 1125-1128). Guanine nucleotide exchange factors (GEFs) and GTPase-activating proteins (GAPs), which regulate the GTP-GDP bound states of the Rho family of GTPases, are important determinants of downstream signalling activated by PAK1 kinases (Zhou, K. et al. (1998) J. Biol. Chem., 273, 16782-16786).

The nucleic acid sequence and the amino acid sequence of PAK1 are shown in SEQ ID NO: 1 and 2, respectively. The sequences of PAK1 required for tight binding to Cdc42 and Rac have been studied by analyzing properties of truncated fragments and site-directed mutants as well as by determining the solution structure of a complex of Cdc42 with the homologous segment of WASP (Burbelo, P.D. et al. (1995) J. Biol. Chem., 270, 29071-29074; Rudolph, M.G. et al. (1998) J. Biol. Chem., 273, 18067-18076; Abdul-Manan, N. et al. (1999) Nature, 399, 379-383). Overlapping but not coincident with the PBD (p21-binding-domain) of PAK1 is a segment implicated in autoinhibition (Zhao, Z. S. et al. (1998) Mol. Cell Biol, 18, 2153-2163; Lei, M. et al. (2000) Cell, 102, 387-397). This autoregulatory region includes the inhibitory switch and kinase inhibitory domains, that interfere with kinase autoactivation (Lei, M. et al. (2000) Cell 102, 387-397). Mutations within the autoregulatory region yield constitutively-active mutants (Zhao, Z. S. et al. (1998), supra; Lei, M. et al. (2000) supra). Expression of the autoregulatory domain including aminoacids 83-149 (PID for PAK inhibitory domain) of PAK1 in mammalian cells prevents the activation of downstream effectors through PAK1. Thus, coexpression of this PAK inhibitor with the constitutively-active GTPase $Cdc42^{G12V}$, an activator of PAK1, prevented e.g. the formation of peripheral actin microspikes and associated loss of stress fibers normally induced by this p21-protein (Zhao, Z. S. et al. (1998), supra).

In a recent reports, inhibition of PAK1 activity in breast cancer cells was associated with a reduction in c-Jun N-terminal kinase activity, inhibition of DNA binding activity of transcription factor AP-1 and suppression of in vivo transcription driven by AP-1 promoter which is known to be involved in breast cancer invasion (Adam, L. et al. (2000) J. Biol. Chem., 275, 12041-12050). Furthermore, Ngo, the etiologic agent of gonorrhea, induces the activation of proinflammatory cytokines via a cascade of cellular stress response kinases involving PAK, which directs the signal from the Rho family of small GTPases to JNK and AP-1 activation (Naumann, M. et al. (1998) J. Exp. Med., 188, 1277-1286). However, there has been no report about a potential role for PAK family kinases in a joint disease such as osteoarthritis.

DESCRIPTION OF DRAWINGS

One subject matter of the present invention is, therefore, the use of a PAK inhibitor for the treatment of a joint disease, in particular a degenerative joint disease such as osteoarthritis and/or an inflammatory joint disease such as rheumatoid arthritis. The PAK inhibitor can also be used to treat the joint pain, in particular by reducing the joint pain in degenerative joint diseases. In addition, a PAK inhibitor can be used for the production of a medicament for the treatment of a joint disease and/or for the treatment of the joint pain as specified above.

According to the present invention the term "inhibitor" refers to a biochemical or chemical compound which preferably inhibits or reduces the serine/threonine kinase activity of PAK or the expression of the PAK gene or the localization of PAK in the cell, as e.g. described in Kiosses, W. B. et al. (2002) Circ. Research, Apr. 5, 2002, 697-702. The serine/threonine kinase activity can be measured according to standard protocols, e.g. with the HitHunter™ Serine/Threonine Kinase Assay of Applied Biosystems, Inc., Foster City, Calif., U.S.A. The expression of the PAK gene can be measured by RT-PCT or Western blot analysis as described in the examples of the present invention.

Figures 1A, 1B, 1C:
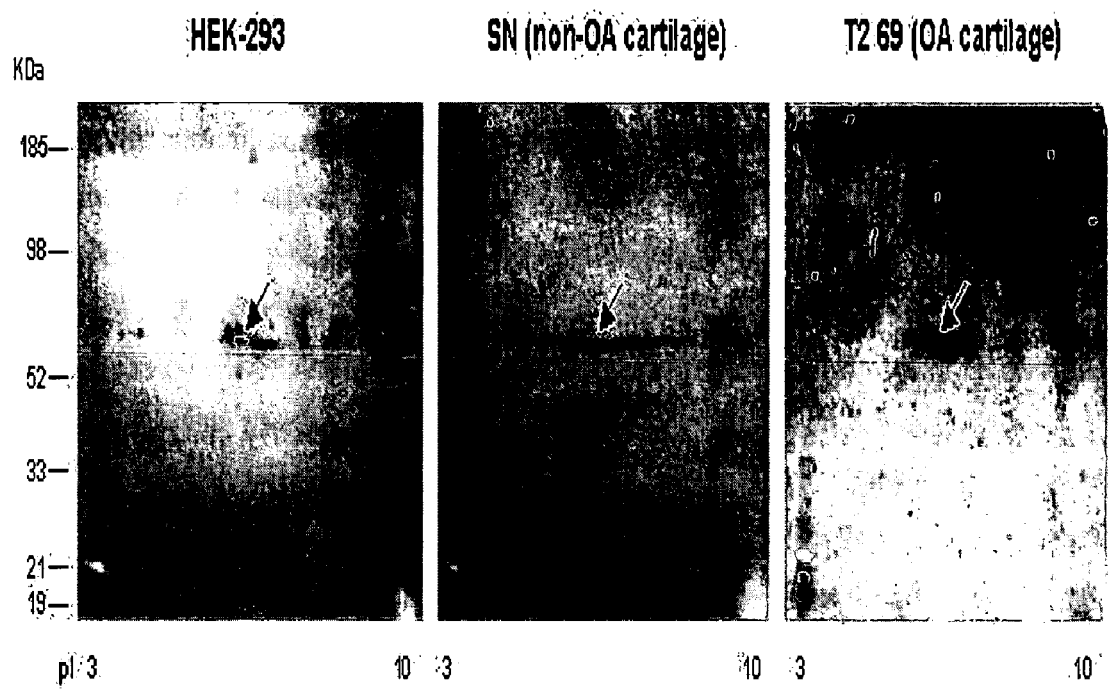

The term "PAK" refers to a family of serine/threonine p21-activating kinases including, without limitation, PAK1, PAK2, PAK3 and/or PAK4. These proteins preferably serve as targets for the small GTP binding proteins Cdc42 and Rac as described above. In particular, the term "PAK" refers to human PAK, especially human PAK1. The nucleic acid and amino acid sequences of human PAK1 are shown in SEQ ID NO: 1 and 2, respectively. The amino acid sequences of human PAK 2, 3 and 4 are shown in SEQ ID NO: 3, 4 and 5, respectively. The gene sequences coding for these human PAKs can easily be derived by using the genetic code. The gene bank accession numbers for human PAK 1, 2, 3 and 4 are NP_002567, Q13177, NP_002569 and NP_005875, respectively. The non-human homologs can be isolated by means of the human PAK 1, 2, 3 or 4 gene sequences with methods known to a person skilled in the art, e.g. through PCR amplification or hybridization under stringent conditions (e.g. 60° C. in 2.5×SSC buffer followed by several washing steps at 37° C. in a lower buffer concentration) with suitable probes derived from e.g. the human PAK sequences according to standard laboratory methods.

Examples of such PAK inhibitors are the PAK1 inhibitor domain with the amino acid sequence HTIHVGFDAV TGEFTGMPEQ WARLLQTSNI TKSEQKKNPQ AVLDVLEFYN SKKTSNSQKY MSFTDKS (SEQ ID NO: 6), the PAK1 peptide with the amino acid sequence KPPAPPM-RNT STM (SEQ ID NO: 7), the Tat-PAK fusion peptide with the amino acid sequence YGRKKRRQRR RGKPPA-PPMR NTSTM (SEQ ID NO: 8), binding proteins or binding peptides directed against PAK, in particular against the active site of PAK, nucleic acids directed against the PAK gene or PAK itself, a chemical molecule, preferably a small molecule, and/or a natural product extract.

According to the present invention the term "chemical molecule" encompasses non-polymeric organic compounds, lipids, carbohydrates, peptides, preferably peptides with about 10 to about 80 amino acids, in particular with 10 to 25 amino acids and oligonucleotides, preferably with about 10 to about 90 nucleotides, in particular with 15 to 25 nucleotides. Especially preferred are small chemical molecules, in particular non-polymeric organic compounds, either synthesized in a laboratory or found in nature, with a preferred molecular weight of about 200 g/mole to about 1500 g/mole, in particular 400 g/mole to 1000 g/mole.

Alternatively the inhibitor of the present invention can be in the form of a natural product extract, either in crude or in purified form. The extract can be produced according to standard procedures, such as water and/or alcohol and/or organic solvent extraction and/or column chromatography and/or precipitation from an animal, plant or microbial source, like snake poison, leaves or microbial fermentation broths.

The term "binding protein" or "binding peptide" refers to a class of proteins or peptides which bind and inhibit RAK including, without limitation, polyclonal or monoclonal antibodies, antibody fragments and protein scaffolds directed against PAK, e.g. anticalins which are directed against PAK.

The procedure for preparing an antibody or antibody fragment is effected in accordance with methods which are well known to the skilled person, e.g. by immunizing a mammal, for example a rabbit, with PAK, where appropriate in the presence of, for example, Freund's adjuvant and/or aluminium hydroxide gels (see, for example, Diamond, B.

A. et al. (1981) The New England Journal of Medicine: 1344-1349). The polyclonal antibodies which are formed in the animal as a result of an immunological reaction can subsequently be isolated from the blood using well known methods and, for example, purified by means of column chromatography. Monoclonal antibodies can, for example, be prepared in accordance with the known method of Winter & Milstein (Winter, G. & Milstein, C. (1991) Nature, 349, 293-299).

According to the present invention the term antibody or antibody fragment is also understood as meaning antibodies or antigen-binding parts thereof, which have been prepared recombinantly and, where appropriate, modified, such as chimaeric antibodies, humanized antibodies, multifunctional antibodies, bispecific or oligospecific antibodies, single-stranded antibodies and F(ab) or F(ab)$_2$ fragments (see, for example, EP-B1-0 368 684, U.S. Pat. Nos. 4,816, 567, U.S. Pat. No. 4,816,397, WO 88/01649, WO 93/06213 or WO 98/24884).

As an alternative to the classical antibodies it is also possible, for example, to use protein scaffolds against PAK, e.g. anticalins which are based on lipocalin (Beste et al. (1999) Proc. Natl. Acad. Sci. USA, 96, 1898-1903). The natural ligand-binding sites of the lipocalins, for example the retinol-binding protein or the bilin-binding protein, can be altered, for example by means of a "combinatorial protein design" approach, in such a way that they bind to selected haptens, here to PAK (Skerra, 2000, Biochim. Biophys. Acta, 1482, 337-50). Other known protein scaffolds are known as being alternatives to antibodies for molecular recognition (Skerra (2000) J. Mol. Recognit., 13, 167-187).

The term "nucleic acids against the PAK gene or PAK itself" refers to double-stranded or single stranded DNA or RNA which, for example, inhibit the expression of the PAK gene or the activity of PAK and includes, without limitation, antisense nucleic acids, aptamers, siRNAs (small interfering RNAs) and ribozymes.

The nucleic acids, e.g. the antisense nucleic acids, can be synthesized chemically, e.g. in accordance with the phosphotriester method (see, for example, Uhlmann, E. & Peyman, A. (1990) Chemical Reviews, 90, 543-584). Aptamers are nucleic acids which bind with high affinity to a polypeptide, here PAK. Aptamers can be isolated by selection methods such as SELEX (see e.g. Jayasena (1999) Clin. Chem., 45, 1628-50; Klug and Famulok (1994) M. Mol. Biol. Rep., 20, 97-107; U.S. Pat. No. 5,582,981) from a large pool of different single-stranded RNA molecules. Aptamers can also be synthesized and selected in their mirror-image form, for example as the L-ribonucleotide (Nolte et al. (1996) Nat. Biotechnol., 14, 1116-9; Klussmann et al. (1996) Nat. Biotechnol., 14, 1112-5). Forms which have been isolated in this way enjoy the advantage that they are not degraded by naturally occurring ribonucleases and, therefore, possess greater stability.

Nucleic acids may be degraded by endonucleases or exonucleases, in particular by DNases and RNases which can be found in the cell. It is, therefore, advantageous to modify the nucleic acids in order to stabilize them against degradation, thereby ensuring that a high concentration of the nucleic acid is maintained in the cell over a long period of time (Beigelman et al. (1995) Nucleic Acids Res. 23:3989-94; WO 95/11910; WO 98/37240; WO 97/29116). Typically, such a stabilization can be obtained by introducing one or more internucleotide phosphorus groups or by introducing one or more non-phosphorus internucleotides.

Suitable modified internucleotides are compiled in Uhlmann and Peyman (1990), supra (see also Beigelman et al. (1995) Nucleic Acids Res. 23:3989-94; WO 95/11910; WO 98/37240; WO 97/29116). Modified internucleotide phosphate radicals and/or non-phosphorus bridges in a nucleic acid which can be employed in one of the uses according to the invention contain, for example, methyl phosphonate, phosphorothioate, phosphoramidate, phosphorodithioate and/or phosphate esters, whereas non-phosphorus internucleotide analogues contain, for example, siloxane bridges, carbonate bridges, carboxymethyl esters, acetamidate bridges and/or thioether bridges. It is also the intention that this modification should improve the durability of a pharmaceutical composition which can be employed in one of the uses according to the invention.

The use of suitable antisense nucleic acids is further described e.g. in Zheng and Kemeny (1995) Clin. Exp. Immunol., 100, 380-2; Nellen and Lichtenstein (1993) Trends Biochem. Sci., 18, 419-23, Stein (1992) Leukemia, 6, 697-74 or Yacyshyn, B. R. et al. (1998) Gastroenterology, 114, 1142).

The production and use of siRNAs as tools for RNA interference in the process to down regulate or to switch off gene expression, here PAK gene expression, is e.g. described in Elbashir, S. M. et al. (2001) Genes Dev., 15, 188 or Elbashir, S. M. et al. (2001) Nature, 411, 494.

Ribozymes are also suitable tools to inhibit the translation of nucleic acids, here the RAK gene, because they are able to specifically bind and cut the mRNAs. They are e.g. described in Amarzguioui et al. (1998) Cell. Mol. Life Sci., 54, 1175-202; Vaish et al. (1998) Nucleic Acids Res., 26, 5237-42; Persidis (1997) Nat. Biotechnol., 15, 921-2 or Couture and Stinchcomb (1996) Trends Genet., 12, 510-5.

Thus, the nucleic acids described can be used to inhibit or reduce the expression of the PAK genes in the cells both in vivo and in vitro and consequently act as a PAK inhibitor in the sense of the present invention. A single-stranded DNA or RNA is preferred for the use as an antisense oligonucleotide or ribozyme, respectively. For the production of the medicament the PAK inhibitors of the present invention are usually formulated with one or more pharmaceutically acceptable additives or auxiliary substances, such as physiological buffer solution, e.g. sodium chloride solution, demineralized water, stabilizers, such as protease or nuclease inhibitors, preferably aprotinin, $\epsilon$-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the medicament is in general adjusted using a suitable organic or inorganic buffer, such as, for example, preferably using a phosphate buffer, tris buffer (tris(hydroxymethyl)aminomethane), HEPES buffer ([4-(2-hydroxyethyl)piperazino]ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The medicament can be administered in a conventional manner, e.g. by means of oral dosage forms, such as, for example, tablets or capsules, by means of the mucous membranes, for example the nose or the oral cavity, in the form of dispositories implanted under the skin, by means of injections, infusions or gels which contain the medicaments according to the invention. It is further possible to administer the medicament topically and locally in order to treat the particular joint disease as described above, if appropriate, in the form of liposome complexes. Furthermore, the treatment can be carried out by means of a transdermal therapeutic system (TTS), which makes possible a temporally controlled release of the medicaments. TTS are known for example, from EP 0 944 398 A1, EP 0 916 336 A1, EP 0 889 723 A1 or EP 0 852 493 A1.

Injection solutions are in general used if only relatively small amounts of a solution or suspension, for example about 1 to about 20 ml, are to be administered to the body. Infusion solutions are in general used if a larger amount of a solution or suspension, for example one or more litres, are to be administered. Since, in contrast to the infusion solution, only a few millilitres are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

The above-described nucleic acids can be used in naked form, in the form of gene transfer vectors or complexed with liposomes or gold particles.

Examples of gene transfer vectors are viral vectors, for example adenoviral vectors or retroviral vectors (Lindemann et al. (1997), Mol. Med., 3, 466-76; Springer et al. (1988) Mol. Cell., 2, 549-58). Complexes with liposomes usually achieve a very high efficiency of transfection, in particular of skin cells (Alexander and Akhurst, 1995, Hum. Mol. Genet. 4:2279-85). In lipofection, small, unilamellar vesicles composed of cationic lipids are prepared by ultrasonicating the liposome suspension. The DNA is bound ionically on the surface of the liposomes in a ratio which is such that a positive net charge remains and all the plasmid DNA is complexed by the liposomes. In addition to the DOTMA (1,2-dioleyloxypropyl-3-trimethylammonium bromide) and DOPE (dioleoylphosphatidylethanolamine) lipid mixtures employed by Felgner, P. L. et al. (1987), Proc. Natl. Acad. Sci USA, 84, 7413-7414, a large number of lipid formulations have by now been synthesized and tested for their efficiency in transfecting a variety of cell lines (Behr et al. (1989) Proc. Natl. Acad. Sci. USA, 86, 6982-6986; Gao and Huang (1991), Biochim. Biophys. Acta, 1189, 195-203; Felgner et al. (1994) J. Biol. Chem., 269, 2550-2561). Examples of the lipid formulations are DOTAP N-[1-(2,3-dioleoyloxy)propyl]-N,N,N-trimethylammonium methyl sulphate or DOGS (dioctadecylamidoglycylspermine).

Auxiliary substances which increase the transfer of nucleic acids into the cell can, for example, be proteins or peptides which are bound to the DNA or synthetic peptide-DNA molecules which enable the nucleic acid to be transported into the nucleus of the cell (Schwartz et al. (1999) Gene Therapy 6:282; Branden et al. (1999) Nature Biotech., 17, 784). Auxiliary substances also include molecules which enable nucleic acids to be released into the cytoplasm of the cell (Planck et al. (1994) J. Biol. Chem., 269, 12918; Kichter et al. (1997) Bioconj. Chem., 8, 213) or, for example liposomes (Uhlmann and Peyman (1990), supra).

Another, particularly suitable form can be obtained by applying the above-described nucleic acids to gold particles and firing these particles into tissue or cells using what is termed a "gene gun" (Wang et al. (1999) J. Invest. Dermatol. 112:775-81, Tuting et al. (1998) J. Invest. Dermatol. 111: 183-8).

Another subject matter of the present invention is the use of PAK or the PAK gene as a target for the discovery of a PAK inhibitor for the treatment of a joint disease, in particular a degenerative joint disease such as osteoarthritis or an inflammatory joint disease such as rheumatoid arthritis, and/or for the treatment of joint pain, in particular by reducing the joint pain in degenerative joint diseases. Preferably the PAK inhibitor can be used in form of a medicament as described above.

Accordingly, the present invention refers also to a method of screening a PAK inhibitor, wherein the method comprises the steps of:
(a) providing PAK or the PAK gene,
(b) providing a test compound, and
(c) measuring or detecting the influence of the test compound on PAK or the PAK gene.

In general, PAK or the PAK gene is provided e.g. in an assay system and brought directly or indirectly into contact with a test compound, in particular a biochemical or chemical test compound, e.g. in the form of a chemical compound library. Then, the influence of the test compound on PAK or the PAK gene is measured or detected. Thereafter, suitable inhibitors can be analyzed and/or isolated. For the screening of chemical compound libraries, the use of high-throughput assays are preferred which are known to the skilled person or which are commercially available.

According to the present invention the term "chemical compound library" refers to a plurality of chemical compounds that have been assembled from any of multiple sources, including chemically synthesized molecules and natural products, or that have been generated by combinatorial chemistry techniques.

In general, the influence of the test compound on PAK or the PAK gene is measured or detected in a heterogeneous or homogeneous assay. As used herein, a heterogeneous assay is an assay which includes one or more washing steps, whereas in a homogeneous assay such washing steps are not necessary. The reagents and compounds are only mixed and measured.

Suitable functional assays may be based on the gene expression of PAK, the direct activation of PAK by GTPases such as Cdc42, Rac1, Wrch-1 or Chp or the complex formation with activated (GTP-bound) p21. In the presence of a biochemical or chemical compound to be tested as an inhibitor of PAK the gene expression, the direct activation or the complex formation with other proteins, e.g. cellular proteins as e.g. specified above, can be measures by means generally known to a skilled person. In general, commercially available kinase assays systems quantitatively detect the amount of phosphate incorporated in a substrate.

For example, the prevention of formation of peripheral actin microspikes and associated loss of stress fibers can be measured as described in Zhao, Z. S. et al. (1998), supra.

Heterogeneous assays are, for example, ELISA, DELFIA, SPA and flashplate assays.

ELISA (enzyme linked immuno sorbent assay)-based assays are offered by various companies. The assays employ random peptides that can be phosphorylated by a kinase, such as PAK. Kinase-containing samples are usually diluted into a reaction buffer containing e.g. ATP and requisite cations and then added to plate wells. Reactions are stopped by simply removing the mixtures. Thereafter, the plates are washed. The reaction is initiated e.g. by the addition of a biotinylated substrate to the kinase. After the reaction, a specific antibody is added. The samples are usually transferred to pre-blocked protein-G plates and after washing e.g streptavidin-HRP is added. Thereafter, unbound streptavidin-HRP (horseradish peroxidase) is removed, the peroxidase colour reaction is initiated by addition of the peroxidase substrate and the optical density is measured in a suitable densitometer.

DELFIA (dissociation enhanced lanthanide fluoro immuno assay)-based assays are solid phase assay. The antibody is usually labelled with Europium or another lanthanide and the Europium fluorescence is detected after having washed away unbound Europium-labelled antibodies.

SPA (scintillation proximity assay) and the flashplate assay usually exploit biotin/avidin interactions for capturing radiolabelled substrates. Generally the reaction mixture includes the kinase, a biotinylated peptide substrate and $\gamma$-[$P^{33}$]ATP. After the reaction, the biotinylated peptides are captured by streptavidin. In the SPA detection, streptavidin is bound on scintillant containing beads whereas in the flashplate detection, streptavidin is bound to the interior of the well of scintillant containing microplates. Once immobilized, the radiolabelled substrate is close enough to the scintillant to stimulate the emission of light.

Alternative homogeneous assays are, for example, TR-FRET, FP, ALPHA and gene assays.

TR-FRET (time-resolved fluorescence resonance energy transfer)-based assays are assays which usually exploit the fluorescence resonance energy transfer between Europium and APC, a modified allophycocyanin or other dyes with overlapping spectra such as Cy3/Cy5 or Cy5/Cy7 (Schobel, U. et al. (1999) Bioconjugate Chem. 10, 1107-1114). After excitation e.g. of Europium with light at 337 nm, the molecule fluoresces at 620 nm. But if this fluorophore is close enough to APC, the Europium will transfer its excitation energy to APC, which fluoresces at 665 nm. The kinase substrate is usually a biotin-labelled substrate. After the kinase reaction, Europium-labelled-(P)-specific antibodies are added along with streptavidin-APC. The phosphorylated peptides bring the Europium-labelled antibody and the streptavidin-APC into close contact. The close proximity of the APC to the Europium fluorophore will cause a quenching of the Europium fluorescence at benefit of the APC fluorescence (FRET).

Fluorescence polarisation (FP)-based assays are assays which use polarized light to excite fluorescent substrate peptides in solution. These fluorescent peptides are free in solution and tumble, causing the emitted light to become depolarised. When the substrate peptide binds to a larger molecule, however, such as (P)-Tyr, its tumbling rates are greatly decreased, and the emitted light remains highly polarized. For a kinase assay there are generally two options:

(a) A fluorescent phosphopeptide tracer is bound to a (P)-specific antibody. Phosphorylated products will compete the fluorescent phosphopeptide from the antibody resulting in a change of the polarisation from high to low.

(b) A phosphorylated substrate peptide binds to the phosphospecific antibody resulting in a change of polarisation from low to high.

ALPHA (amplified luminescent proximity homogenous)-based assays, are assays which rely on the transfer of singlet oxygen between donor and acceptor beads brought into proximity by a phosphorylated peptide. Upon excitation at 680 nm, photosensitisers in donor beads convert ambient oxygen to singlet-state oxygen, which diffuses up to a distance of 200 nm. Chemiluminescent groups in the acceptor beads transfer energy to fluorescent acceptors within the bead, which then emits light at approximately 600 nm.

EFC (enzyme fragment complementation)-based assays or equivalent assays can be used in particular for high-throughput screening of compounds. The EFC assay is based on an engineered β-galactosidase enzyme that consists of two fragments—the enzyme acceptor (EA) and the enzyme donor (ED). When the fragments are separated, there is no β-galactosidase activity, but when the fragments are together they associate (complement) to form active enzyme. The EFC assay utilizes an ED-analyte conjugate in which the analyte may be recognized by a specific binding protein, such as an antibody or receptor. In the absence of the specific binding protein, the ED-analyte conjugate is capable of complementing EA to form active β-galactosidase, producing a positive luminescent signal. If the ED-analyte conjugate is bound by a specific binding protein, complementation with EA is prevented, and there is no signal. If free analyte is provided (in a sample), it will compete with the ED-analyte conjugate for binding to the specific binding protein. Free analyte will release ED-analyte conjugate for complementation with EA, producing a signal dependent upon the amount of free analyte present in the sample.

An example of a gene assay is the two-hybrid system assay (Fields and Sternglanz (1994) Trends in Genetics, 10, 286-292; Colas and Brent (1998) TIBTECH, 16, 355-363). In this test, cells are transformed with expression vectors which are expressing fusion proteins consisting of the polypeptide according to the invention and a DNA-binding domain of a transcription factor such as Gal4 or LexA. The transformed cells additionally contain a reporter gene whose promoter contains binding sites for the corresponding DNA-binding domain. By transforming with another expression vector which is expressing a second fusion protein consisting of a known or unknown polypeptide and an activation domain, for example from Gal4 or herpes simplex virus VP16, the expression of the reporter gene can be greatly increased if the second fusion protein interacts with the polypeptide. Consequently this test system can be used for screening for biochemical or chemical compounds which inhibit an interaction between PAK and e.g. GTPases, such as Cdc42, Rac1, Wrch-1 or Chp, or activated (GTP-bound) p21 (see e.g. Vidal and Endoh (1999) Trends in Biotechnology, 17, 374-81). In this way, it is possible rapidly to identify novel active compounds which can be used for the treatment of joint diseases.

Alternatively, in case the test compound is a protein or peptide, coexpression of this test compound with a GTPase, such as Rac1, Wrch-1, Chp or the constitutively-active Cdc42, as an activator of PAK in the presence of PAK can be used to measure or detect the influence of the test compound on PAK as e.g. described in Zhao, Z. S. et al. (1998), supra).

Another example of a gene assay is a functional assay wherein the activity of the kinase is converted into a functional cellular response such as growth, growth arrest, differentiation or apoptosis. For this type of screening yeast is a particularly suitable model system. For example in a PAK 1-yeast functional assay, when cultured on glucose containing medium, the e.g. PAK 1-yeast cells grow like normal yeast cells. When, however, being exposed to galactose, the intracellular expression of PAK 1 is induced causing the yeast cell to die. Compounds that inhibit PAK 1 activity prevent the cell death in this case.

Another assay is based on solid phase-bound polypeptides such as PAK, GTPases, such as Cdc42, Rac1, Wrch-1 or Chp, or activated (GRP-bound) p21 and the interference with the compounds to be tested. Thus, a test compound, for example, contain a detectable marker, for example, the compound can be radioactively labelled, fluorescence-labelled or luminescence-labelled as already explained above. Furthermore, compounds can be coupled to proteins which permit indirect detection, for example by means of enzymatic catalysis employing a peroxidase assay which uses a chromogenic substrate or by means of binding a detectable antibody. Another possibility is that of investigating the solid phase-bound protein complexes by means of mass spectrometry (SELDI). Changes in the conformation of e.g. PAC or the other proteins described above as the result of interaction with a test substance can be detected, for example, by the change in the fluorescence of an endogenous tryptophan residue in the polypeptide.

The solid phase-bound polypeptides can also be part of an array. Methods for preparing such arrays using solid phase chemistry and photolabile protecting groups are disclosed, for example, in U.S. Pat. No. 5,744,305. These arrays can also be brought into contact with test compound or compound libraries and tested for interaction, for example binding or changing conformation.

In another embodiment of the present invention, the method is carried out using whole cells. Usually cells growing at the bottom of multiwell plates are fixed and permeabilized, blocked and incubated with e.g. a primary (P)-specific antibody against the substrate of interest. Then, e.g. Europium labelled or HRP conjugated secondary antibodies in conjunction with specific chemiluminescent or calorimetric substances, e.g. as described above, are utilized to generate the signal. In combination with the use of a microscope not only the amount of (P)-specific antibodies can be quantified on the single cell level, but also phosphorylation-induced translocations of a substrate or morphological changes of the cells.

Advantageously the method of the present invention is carried out in a robotics system e.g. including robotic plating and a robotic liquid transfer system, e.g. using microfluidics, i.e. channelled structured.

In another embodiment of the present invention, the method is carried out in form of a high-through put screening system. In such a system advantageously the screening method is automated and miniaturized, in particular it uses miniaturized wells and microfluidics controlled by a roboter.

In another embodiment the present invention refers also to a method for producing a medicament for the treatment of a joint disease, in particular a degenerative joint disease such as osteoarthritis or an inflammatory joint disease such as rheumatoid arthritis, and/or for the treatment of a joint pain, in particular by reducing the joint pain in degenerative joint diseases, wherein the method comprises the steps of:
(a) carrying out the method according to any of the claims 13 to 19,
(b) isolating a measured or detected test compound suitable for the treatment of a joint disease and/or a joint pain, and
(c) formulating the measured or detected test compounds with one or more pharmaceutically acceptable carriers or auxiliary substances, e.g. as described above.

The following Figures, Sequences and Examples shall explain the present invention without limiting the scope of the invention.

DESCRIPTION OF THE FIGURES

FIGS. 1A-C show the Expression of PAK1 in extracts of HEK293 cells and in human primary chondrocytes.

Extracts of human HEK293 cells as well as human primary chondrocytes originating from cartilage of osteoarthritis patients and control cartilage were separated by 2-dimensional gel electrophoresis. Proteins were transferred to PVDF membranes by Western blotting and PAK1 was detected by a specific antibody.

Figure 2:
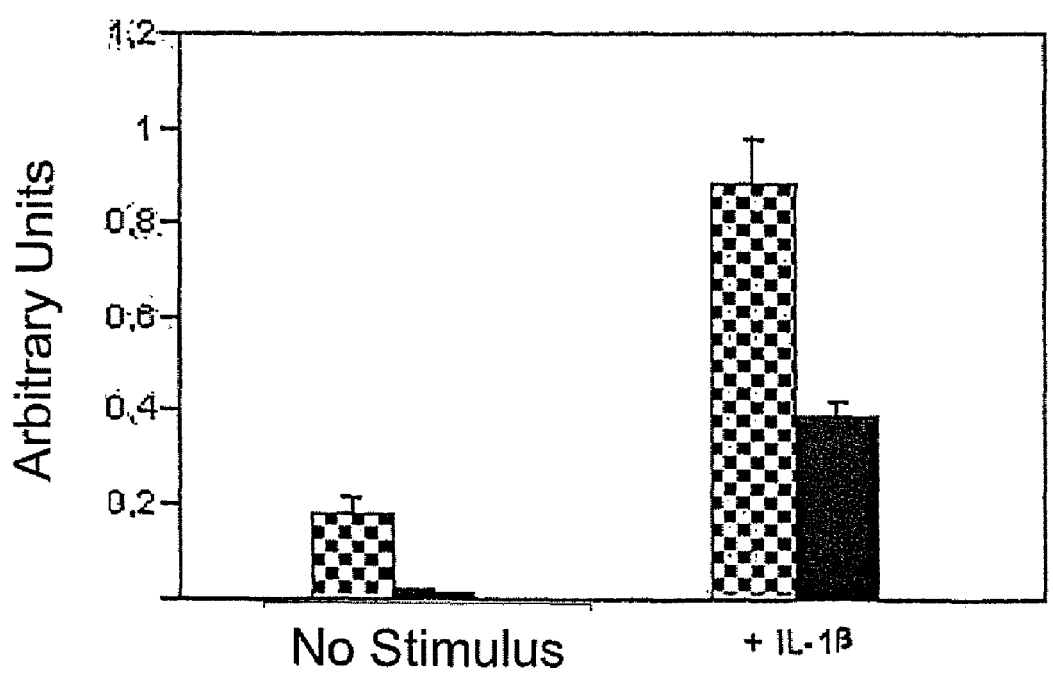

FIG. 2 shows that the overexpression of the PAK1-ID repressed the IL-1β induced expression of MMP13 in human SW1353 cells.

The PAK1 inhibitory domain was subcloned into the pCEP4 vector and transfected into SW1353 cells. Where indicated, IL-1β was used as a stimulus at a concentration of 10 ng/ml for 24 h. Supernatants were collected and the amount of MMP13 protein was determined by ELISA. Values are shown in arbitrary units and represent at least 3 independent results ±SD. The chequered column represents the experiments with the vector pCEP4 (void vector) and the black column represents the experiments with the vector pCEP4_PAK1-ID.

Figure 3:
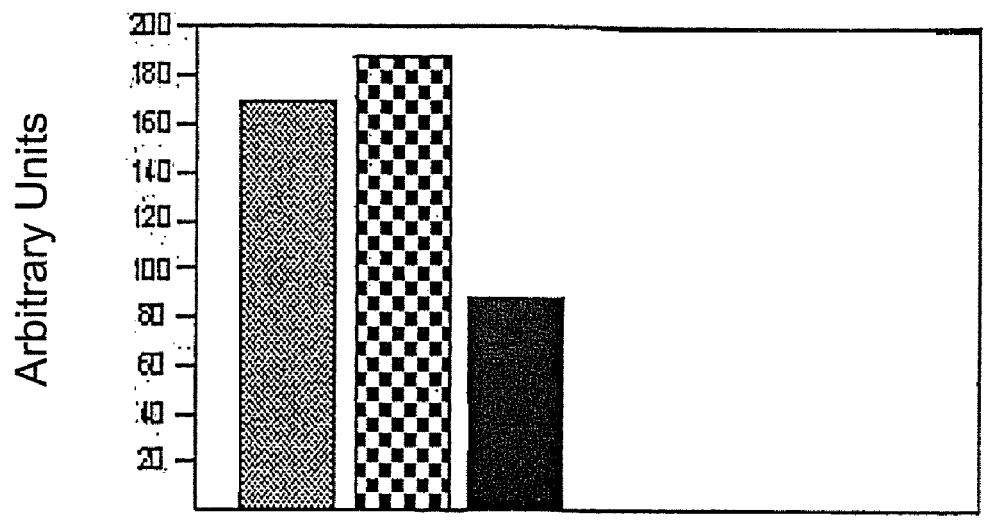

FIG. 3 shows that overexpression of the PAK1-ID repressed the IL-1β induced expression of PGE2 in human SW1353 cells.

The PAK1 inhibitory domain was subcloned into the pCEP4 vector and transfected into SW1353 cells. Cells were stimulated with a combination of IL-1β and TNFα both at a concentration of 10 ng/ml for 24 h. Supernatants were collected and the amount of MMP13 protein was determined by ELISA. Values in arbitrary units represent the mean of two experiments. The punctured column represents the experiments with no vector plus IL1β and TNFα. The chequered column represents the experiments with the vector pCEP4 (void vector) plus IL1β and TNFα. The black column represents the experiments with the vector pCEP4_PAK1-ID plus IL1β and TNFα.

Figure 4:
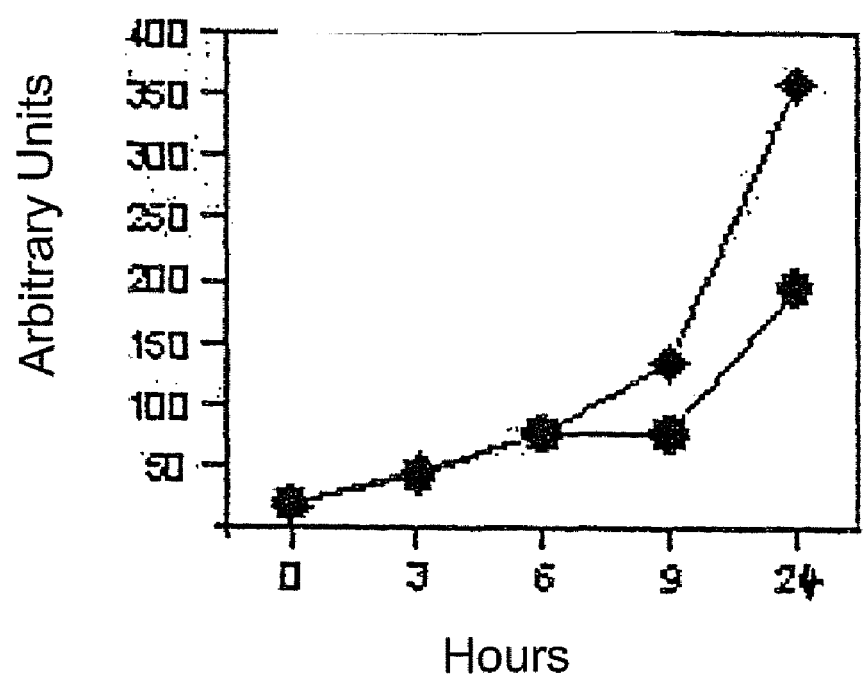

FIG. 4 shows that overexpression of the PAK1-ID represses the IL-1β induced expression of IL-8 in human HEK293 cells.

The PAK1 inhibitory domain subcloned into the pCDNA3.1 vector was transiently transfected into HEK293 cells. Cells were stimulated with IL-1β at a concentration of 10 ng/ml for the indicated time periods. Supernatants were collected and the amount of IL-8 protein was determined by ELISA. Values in arbitrary units represent the mean of two experiments. The circles represents the experiments with the vector pCDNA3.1_PAK1-ID plus IL-1β and the squares represent the experiments with the vector pCDNA3.1 (void vector) plus IL-1β.

DESCRIPTION OF THE SEQUENCES

SEQ ID NO: 1 shows the nucleic acid sequence of PAK1.
SEQ ID NO: 2 shows the amino acid sequence of PAK1.
SEQ ID NO: 3 shows the amino acid sequence of PAK2.
SEQ ID NO: 4 shows the amino acid sequence of PAK3.

SEQ ID NO: 5 shows the amino acid sequence of PAK4.

SEQ ID NO: 6 shows the amino acid sequence of the PAK1 inhibitor domain (PAK1-ID).

SEQ ID NO: 7 shows the amino acid sequence of a proline-rich inhibitor sequence of PAK1 according to Kiosses, W. B. (2002), supra.

SEQ ID NO: 8 shows the amino acid sequence of a synthetic peptide containing the PAK1 proline-rich sequence fused to the polybasic sequence from the HIV tat protein according to Kiosses, W. B. (2002), supra.

SEQ ID NO: 9 shows a first PCR primer for the targeting of conserved sequences between human and mouse PAK1 cDNAs.

SEQ ID NO: 10 shows a second PCR primer for the targeting of conserved sequences between human and mouse PAK1 cDNAs.

SEQ ID NO: 11 shows a first PCR primer for the amplification of the PAK1-ID.

SEQ ID NO: 12 shows a second PCR primer for the amplification of the PAK1-ID.

EXAMPLES

1. Methods 1.1 Reverse Transcription-Polymerase Chain Reaction (RT-PCR)

Total RNA (1 µg) was first digested with 1 unit of RNase-free DNase I to avoid contamination by genomic DNA. DNase I-treated RNA was then reverse-transcribed to cDNA using Thermoscript reverse transcriptase (Life Technologies, Inc.) primed with oligo(dT)20 according to the procedure supplied by the manufacturer. PCR was performed using 5'-TGGCTGGAGGCTCCTTGACA-3'(SEQ ID NO: 9) and 5'-GAGGGCTTGGCMTCTTCAGGA-3' (SEQ ID NO: 10) as primers (MWG Biotech AG, Germany) to target conserved sequences between human and mouse PAK1 cDNAs. PCR conditions were 95° C./30 s, 60° C./30 s and 72° C./45 s for 25 cycles using 2.6 units of Expand High Fidelity PCR DNA polymerase (Roche Diagnostics GmbH, Germany) per 50-µl reaction 1.2 Design of Vector Constructs The polypeptide encoding PAK1 residues 83 to 149 identified as autoinhibitory domain of PAK1 (Zhao, Z. S. et al. (1998), supra) was amplified by PCR. The primers used for amplification were

5'ATCGCCACCATGTACCCTTATGATGTGCCAGA (SEQ ID NO: 11)

TTATGCCCACACAATTCATGTCGGTTTTG-3'

(Kozak sequence is underlined, hemagglutinin (HA) tag is in bold) and 5'-ATCTTATGACTTATCTGTAAAGCTCATG-3'(SEQ ID NO: 12) (MWG, Biotech AG, Germany). PCR conditions were 95° C./30 s, 60° C./30s and 72° C./30 s for 25 cycles using 2.6 units of Expand High Fidelity PCR DNA polymerase (Roche Diagnostics GmbH, Germany) per 50-µl reaction. The PCR product was subcloned into the pCR-TOPO2.1 vector (Invitrogen GmbH, Germany). The HA tagged-PAK1 was introduced into the HindIII and XbaI sites of the mammalian pcDNA3.1 (Invitrogen GmbH, Germany). The PAK1-ID was inserted into the pCEP4 plasmid (Invitrogen GmbH, Germany) via a 5'HindIII and a 3'NotI restriction site. All plasmids were verified by sequencing.

1.3 Cell Culture

Cultures of human SW1353 chondrosarcoma were grown in Dulbecco's modified Eagles's medium (DMEM) containing 10% fetal calf serum (FCS) and penicillin/streptomycin (37° C., 5% CO2). For transfections, 6×104/well were cultured overnight and at the next day transfected with 2 µg DNA and 10 µl GenePORTER™ Transfection Reagent (Gene Therapy Systems, Inc., San Diego, Calif., U.S.A.). After 3 h, an equal volume of medium containing 20% FCS was added and incubated overnight. In the case of overexpression with the pCEP4 vector (Invitrogen GmbH, Germany), two days after transfection the cells were selected with 200 µg/ml hygromycin B (Invitrogen GmbH, Germany). The transfection efficiency was examined with a FACScan (Becton Dickinson Immunocytometry Systems, Inc., Mountain View, Calif., U.S.A.) and on an inverted fluorescence microscope. For most experiments, 60000 cells were transferred into each well of a 35 mm 6-well plate. Prior to stimulation the cells were washed with phosphate buffered saline (PBS) and cultivated for 30 min in DMEM without FCS. For the experiment, the cells were placed for 24 h in 1 ml serum-free DMEM, with or without 10 ng/ml human IL-1β (Roche Diagnostics GmbH Germany) and with or without 10 ng/ml TNFα (Roche Diagnostics GmbH, Germany).

Human embryonic kidney (HEK) 293 were maintained in Dulbecco's modified Eagle's medium supplemented with 10% fetal calf serum. For transfection experiments, cells were seeded at $5 \times 10^5$ cells per well into 6-well dishes 24 h before transfection. Cells were incubated for 4 h in 1.0 ml of serum-free medium containing 20 µl of lipofectAMINE® (Life Technologies, Inc., U.S.A.) and 5.0 µg of total DNA per well (pcDNA3.1-PAK1(83-149) plasmid or pcDNA.1 empty vector used as control). Cells were either left untreated or stimulated with interleukin-1β (10 ng/ml; R&D Systems, Inc., Minneapolis, Minn., U.S.A.) following a period of recovery (16 h) in medium containing 10% fetal calf bovine. Culture supernatant were removed and expression of IL-8 (R&D Systems, Inc., Minneapolis, Minn., U.S.A.), PGE2 (SpiBiom Inc.), and MMP-13 (Amersham Pharmacia Biotech, Inc.) was monitored by ELISA according to the procedure supplied by the manufacturer.

1.4 Western Blot Analysis and ELISA

To assess the expression of the HA-tagged $PAK^{183-149}$ peptides, cells were lysed into 100µl of Lysis Buffer (20 mM MOPS, 2 mM EGTA, 5 mM EDTA, 0,5% Nonidet P-40 supplemented by complete EDTA-free protease inhibitor cocktail (Roche Diagnostics GmbH, Germany), and protein concentration was determined using BCA Protein assay kit (Pierce Biotechnology, Inc. Rockford, Ill., U.S.A.). Proteins were separated by 4-12% NuPAGE gel (Invitrogen GmbH, Germany) before transfer to PVDF membrane (Millipore Corp., U.S.A.).

Protein extracts from human primary chondrocytes from osteoarthritis-affected patient tissue as well as from normal tissue were prepared according to standard techniques. Expression of PAK1 was investigated by two-dimensional gel electrophoresis and immunoblotting using 30 µg of proteins. For 2D-gel electrophoresis, isoelectric focusing was performed using linear 7-cm immobilized pH 3-10 gradient IPG strips (Bio-Rad Laboratories, Inc., U.S.A.) on a protein IEF Cell (Bio-Rad Laboratories, Inc., U.S.A.). The final focusing step was at 4000 V for 8 h. The second dimension was performed on NuPAGE Novex 4-12% ZOOM Gel (Invitrogen GmbH, Germany) and the proteins were transferred on PVDF membrane (Millipore Corp., U.S.A.).

For immunoblotting, HA-tagged PAK[183-149] and PAK1 proteins were detected using HA-tag polyclonal antibody (BD Biosciences Clontech, Palo Alto, Calif., U.S.A.) and αPAK(N-20) polyclonal antibody (Santa Cruz), respectively. Briefly, membranes were blocked with TBS-T (150 mM NaCl, 20 mM Tris, pH 7.6, 0.1% Tween 209 containing 5% fat-free dried milk for 1 h at room temperature; incubated in TBS-T containing either a 1/500 dilution of HA-tag antibody or a 1/50 dilution of αPAK(N-20) antibodies for 1 h at RT, and finally incubated in TBS-T containing 1/10000 anti-rabbit horseradish peroxydase-conjugated antibody (Pierce) for 1 h. Membranes were processed using ECL according to the manufacturer's instructions (Amersham Pharmacia Biotech, Inc.).

For the analysis of MMP13, IL-8 and PGE2 protein levels, supernatants of cell cultures were determined by ELISA for MMP13 (Amersham Pharmacia Biotech, Inc.), IL-8 (R&D Systems, Inc. Minneapolis, Minn., U.S.A.) and PGE2 (SpiBio) as described by the supplier.

2. Results 2.1 PAK1 Expression in Human Chondrosarcoma Cell Lines and in Mouse Primary Chondrocytes Using RT-PCR, the expression of PAK1 in human SW1353 chondrocyte cell lines, as well as in mouse primary cells stimulated or non-stimulated with retinoic acid were analyzed.

The results obtained in this experiment clearly demonstrate that PAK1 is expressed in the human SW1353 chondrosarcoma cell line, as well as in mouse primary chondrocytes. In a further set of experiments RT-PCR was used to confirm expression of PAK1 in the human CH8 chondrocyte cell line.

The results shown on RNA level have been confirmed also on protein level by using Western blot analysis with a specific antibody for PAK1 (FIG. 1).

Taken together, the results on RNA and protein level confirm that PAK1 is expressed in human and mouse chondrocyte cell lines and primary chondrocytes.

2.2 Interference of the Expression of the Inhibitory Domain of PAK1 with IL-1 Signalling:

MMP13 (matrix metalloproteinase 13) represents an important marker protein for the IL-1 induced expression of proteins that are relevant for osteoarthritis. The PAK1 inhibitory domain (PAK1-ID) in the human chondrosarcoma cell line SW1353 was overexpressed in order to study the requirement for PAK1 for transmission of the signal that leads from IL-1 to the induction of MMP13 expression (FIG. 2).

In transfected as well as in non-transfected SW1353 cells, exposure to IL-1β led to a large increase in the expression and release of MMP13 into the medium. The results of this experiment clearly demonstrated that overexpression of the PAK1-ID inhibits the IL-1β-induced expression of MMP13 in the human SW1353 chondrocyte cell line by ~55%. Furthermore, a basal level of MMP13 secretion into the medium could be observed in transfected as well as in non-transfected SW1353 cells. Expression of the PAK1-ID can inhibit the IL-1β-induced expression of MMP13 in these non-stimulated cells by >80%. Taken together, the results confirm that PAK1 is required for the IL-1β induced expression of MMP13.

Another important marker gene is the prostaglandine PGE2. The regulation of PGE2 expression in SW1353 cells was analyzed in the presence and absence, respectively, of the PAK1-ID (FIG. 3).

Like seen for the inhibition of MMP13 expression, these results confirmed that inhibition of PAK1 through overexpression of the PAK1-ID leads to a significant down-regulation of the IL-1β induced signalling pathways. IL-1β induced expression of PGE2 was inhibited by more than 50% in the SW1353 cell line. Furthermore, regulation of PGE2 indicates an involvement for PAK1 in the processes that are associated with pain in osteoarthritis.

In addition to it's effect in SW1353 cells we investigated the effect of the PAK1-ID, i.e. the interference with PAK1 activity by it's biological inhibitor also in the human embryonic kidney HEK293 cell line (FIG. 4).

The result of this experiment confirmed the findings obtained in the studies in SW1353 cells. PAK1 plays an essential role in the regulation of the signalling cascade that are induced by IL-1β and lead from the activation of the IL-1R down to the activation of transcription factors upregulating the expression of marker genes that are relevant for osteoarthritis and pain such as MMP13, IL-8, and PGE2.

We claim:

1. A method of treating a subject having a degenerative joint disease or an inflammatory joint disease comprising administering to said subject pharmaceutical composition that specifically inhibits p21-activated kinase 1 (PAK1).

2. The method according to claim 1, wherein said degenerative joint disease is osteoarthritis.

3. The method according to claim 1, wherein said inflammatory joint disease is rheumatoid arthritis.

4. The method of claim 1 wherein said PAK1 is human PAK1 of SEQ ID NO: 2.

5. The method according to claim 4, wherein said PAK1 inhibitor has the PAK1 inhibitor domain with the amino acid sequence HTIHVGFDAV TGEFTGMPEQ WARLLQTSNI TKSEQKKNPQ AVLDVLEFYN SKKTSNSQKY MSFTDKS (SEQ ID NO: 6).

* * * * *

SEQUENCE LISTING

```
<160> NUMBER OF SEQ ID NOS: 12

<210> SEQ ID NO 1
<211> LENGTH: 1638
<212> TYPE: DNA
<213> ORGANISM: Homo sapiens

<400> SEQUENCE: 1
atgtcaaata acggcctaga cattcaagac aaaccccag cccctccgat gagaaatacc      60
agcactatga ttggagccgg cagcaaagat gctggaaccc taaccatgg ttctaaacct     120 ctgcctccaa acccagagga gaagaaaaag aaggaccgat tttaccgatc cattttacct    180
ggagataaaa caaataaaaa gaaagagaaa gagcggccca agatttctct cccttcagat   240
tttgaacaca caattcatgt cggttttgat gctgtcacag gggagtttac cggaatgcca    300
```

-continued

```
gagcagtggg cccgcttgct tcagacatca aatatcacta agtcggagca agaagaaaaac   360 ccgcaggctg ttctggatgt gttggagttt tacaactcga agaagacatc caacagccag   420
aaatacatga gctttacaga taagtcagct gaggattaca attcttctaa tgccttgaat   480
gtgaaggctg tgtctgagac tcctgcagtg ccaccagttt cagaagatga ggatgatgat   540
gatgatgatg ctaccccacc accagtgatt gctccacgcc cagagcacac aaaatctgta   600
tacacacggt ctgtgattga accacttcct gtcactccaa ctcgggacgt ggctacatct   660
cccatttcac ctactgaaaa taacaccact ccaccagatg ctttgaccct taatactgag   720
aagcagaaga agaagcctaa aatgtctgat gaggagatct ggagaaaatt acgaagcata   780
gtgagtgtgg gcgatcctaa gaagaaatat acacggtttg agaagattgg acaaggtgct   840
tcaggcaccg tgtacacagc aatggatgtg ccacaggac aggaggtggc cattaagcag   900
atgaatcttc agcagcagcc caagaaagag ctgattatta tgagatcct ggtcatgagg   960 gaaaacaaga acccaaacat tgtgaattac ttggacagtt acctcgtggg agatgagctg   1020
tgggttgtta tggaatactt ggctggaggc tccttgacag atgtggtgac agaaacttgc   1080
atggatgaag gccaaattgc agctgtgtgc cgtgagtgtc tgcaggctct ggagtctttg   1140
cattcgaacc aggtcattca cagagacatc aagagtgaca atattctgtt gggaatggat   1200
ggctctgtca agctaactga ctttggattc tgtgcacaga taaccccaga gcagagcaaa   1260
cggagcacca tggtaggaac cccatactgg atggcaccag aggttgtgac acgaaaggcc   1320
tatgggccca aggttgacat ctggtccctg ggcatcatgg ccatcgaaat gattgaaggg   1380
gagcctccat acctcaatga aaaccctctg agagccttgt acctcattgc caccaatggg   1440
accccagaac ttcagaaccc agagaagctg tcagctatct tccgggactt tctgaaccgc   1500
tgtctcgaga tggatgtgga agagaggt tcagctaaag agctgctaca gcatcaattc   1560
ctgaagattg ccaagcccct ctccagcctc actccactga ttgctgcagc taaggaggca   1620
acaaagaaca atcactaa   1638
```

<210> SEQ ID NO 2
<211> LENGTH: 545
<212> TYPE: PRT
<213> ORGANISM: Homo sapiens

<400> SEQUENCE: 2

```
Met Ser Asn Asn Gly Leu Asp Ile Gln Asp Lys Pro Ala Pro Pro
1               5                   10                  15

Met Arg Asn Thr Ser Thr Met Ile Gly Ala Gly Ser Lys Asp Ala Gly
                20                  25                  30

Thr Leu Asn His Gly Ser Lys Pro Leu Pro Asn Pro Glu Glu Lys
            35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
                100                 105                 110

Thr Lys Ser Glu Gln Lys Lys Asn Pro Gln Ala Val Leu Asp Val Leu
            115                 120                 125

Glu Phe Tyr Asn Ser Lys Lys Thr Ser Asn Ser Gln Lys Tyr Met Ser
```

-continued

```
            130                 135                 140
Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
                180                 185                 190

Arg Pro Glu His Thr Lys Ser Val Tyr Thr Arg Ser Val Ile Glu Pro
                195                 200                 205

Leu Pro Val Thr Pro Thr Arg Asp Val Ala Thr Ser Pro Ile Ser Pro
210                 215                 220

Thr Glu Asn Asn Thr Thr Pro Pro Asp Ala Leu Thr Leu Asn Thr Glu
225                 230                 235                 240

Lys Gln Lys Lys Lys Pro Lys Met Ser Asp Glu Ile Leu Glu Lys
                245                 250                 255

Leu Arg Ser Ile Val Ser Val Gly Asp Pro Lys Lys Tyr Thr Arg
                260                 265                 270

Phe Glu Lys Ile Gly Gln Gly Ala Ser Gly Thr Val Tyr Thr Ala Met
                275                 280                 285

Asp Val Ala Thr Gly Gln Glu Val Ala Ile Lys Gln Met Asn Leu Gln
290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
                340                 345                 350

Thr Asp Val Val Thr Glu Thr Cys Met Asp Glu Gly Gln Ile Ala Ala
                355                 360                 365

Val Cys Arg Glu Cys Leu Gln Ala Leu Glu Ser Leu His Ser Asn Gln
                370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
                420                 425                 430

Pro Glu Val Val Thr Arg Lys Ala Tyr Gly Pro Lys Val Asp Ile Trp
                435                 440                 445

Ser Leu Gly Ile Met Ala Ile Glu Met Ile Glu Gly Glu Pro Pro Tyr
450                 455                 460

Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
                485                 490                 495

Phe Leu Asn Arg Cys Leu Glu Met Asp Val Glu Lys Arg Gly Ser Ala
                500                 505                 510

Lys Glu Leu Leu Gln His Gln Phe Leu Lys Ile Ala Lys Pro Leu Ser
                515                 520                 525

Ser Leu Thr Pro Leu Ile Ala Ala Lys Glu Ala Thr Lys Asn Asn
                530                 535                 540

His
545
```

<210> SEQ ID NO 3
<211> LENGTH: 524
<212> TYPE: PRT
<213> ORGANISM: Homo sapiens

<400> SEQUENCE: 3

```
Met Ser Asp Asn Gly Glu Leu Glu Asp Lys Pro Pro Ala Pro Pro Val
1               5                   10                  15

Arg Met Ser Ser Thr Ile Phe Ser Thr Gly Gly Lys Asp Pro Leu Ser
            20                  25                  30

Ala Asn His Ser Leu Lys Pro Leu Pro Ser Val Pro Glu Glu Lys Lys
        35                  40                  45

Pro Arg His Lys Ile Ile Ser Ile Phe Ser Gly Thr Glu Lys Gly Ser
    50                  55                  60

Lys Lys Lys Glu Lys Glu Arg Pro Glu Ile Ser Pro Pro Ser Asp Phe
65                  70                  75                  80

Glu His Thr Ile His Val Gly Phe Asp Ala Val Thr Gly Glu Phe Thr
                85                  90                  95

Gly Met Pro Glu Gln Trp Ala Arg Leu Leu Gln Thr Ser Asn Ile Thr
            100                 105                 110

Lys Leu Glu Gln Lys Lys Asn Pro Gln Ala Val Leu Asp Val Leu Lys
        115                 120                 125

Phe Tyr Asp Ser Asn Thr Val Lys Gln Lys Tyr Leu Ser Phe Thr Pro
    130                 135                 140

Pro Glu Lys Asp Gly Leu Pro Ser Gly Thr Pro Ala Leu Asn Ala Lys
145                 150                 155                 160

Gly Thr Glu Ala Pro Ala Val Val Thr Glu Glu Asp Asp Asp Glu
                165                 170                 175

Glu Thr Ala Pro Pro Val Ile Ala Pro Arg Pro Asp His Thr Lys Ser
            180                 185                 190

Ile Tyr Thr Arg Ser Val Ile Asp Pro Val Pro Ala Pro Val Gly Asp
        195                 200                 205

Ser His Val Asp Gly Ala Ala Lys Ser Leu Asp Lys Gln Lys Lys
    210                 215                 220

Pro Lys Met Thr Asp Glu Glu Ile Met Glu Lys Leu Arg Thr Ile Val
225                 230                 235                 240

Ser Ile Gly Asp Pro Lys Lys Lys Tyr Thr Arg Tyr Glu Lys Ile Gly
                245                 250                 255

Gln Gly Ala Ser Gly Thr Val Phe Thr Ala Thr Asp Val Ala Leu Gly
            260                 265                 270

Gln Glu Val Ala Ile Lys Gln Ile Asn Leu Gln Lys Gln Pro Lys Lys
        275                 280                 285

Glu Leu Ile Ile Asn Glu Ile Leu Val Met Lys Glu Leu Lys Asn Pro
    290                 295                 300

Asn Ile Val Asn Phe Leu Asp Ser Tyr Leu Val Gly Asp Glu Leu Phe
305                 310                 315                 320

Val Val Met Glu Tyr Leu Ala Gly Gly Ser Leu Thr Asp Val Val Thr
                325                 330                 335

Glu Thr Cys Met Asp Glu Ala Gln Ile Ala Ala Val Cys Arg Glu Cys
            340                 345                 350

Leu Gln Ala Leu Glu Phe Leu His Ala Asn Gln Val Ile His Arg Asp
        355                 360                 365

Ile Lys Ser Asp Asn Val Leu Leu Gly Met Glu Gly Ser Val Lys Leu
```

```
                    370                 375                 380
Thr Asp Phe Gly Phe Cys Ala Gln Ile Thr Pro Glu Gln Ser Lys Arg
385                 390                 395                 400

Ser Thr Met Val Gly Thr Pro Tyr Trp Met Ala Pro Glu Val Val Thr
                405                 410                 415

Arg Lys Ala Tyr Gly Pro Lys Val Asp Ile Trp Ser Leu Gly Ile Met
                420                 425                 430

Ala Ile Glu Met Val Glu Gly Glu Pro Pro Tyr Leu Asn Glu Asn Pro
                435                 440                 445

Leu Arg Ala Leu Tyr Leu Ile Ala Thr Asn Gly Thr Pro Glu Leu Gln
450                 455                 460

Asn Pro Glu Lys Leu Ser Pro Ile Phe Arg Asp Phe Leu Asn Arg Cys
465                 470                 475                 480

Leu Glu Met Asp Val Glu Lys Arg Gly Ser Ala Lys Glu Leu Leu Gln
                485                 490                 495

His Pro Phe Leu Lys Leu Ala Lys Pro Leu Ser Ser Leu Thr Pro Leu
                500                 505                 510

Ile Met Ala Ala Lys Glu Ala Met Lys Ser Asn Arg
                515                 520

<210> SEQ ID NO 4
<211> LENGTH: 544
<212> TYPE: PRT
<213> ORGANISM: Homo sapiens

<400> SEQUENCE: 4

Met Ser Asp Gly Leu Asp Asn Glu Glu Lys Pro Pro Ala Pro Pro Leu
1               5                   10                  15

Arg Met Asn Ser Asn Asn Arg Asp Ser Ser Ala Leu Asn His Ser Ser
                20                  25                  30

Lys Pro Leu Pro Met Ala Pro Glu Glu Lys Asn Lys Lys Ala Arg Leu
                35                  40                  45

Arg Ser Ile Phe Pro Gly Gly Gly Asp Lys Thr Asn Lys Lys Lys Glu
        50                  55                  60

Lys Glu Arg Pro Glu Ile Ser Leu Pro Ser Asp Phe Glu His Thr Ile
65                  70                  75                  80

His Val Gly Phe Asp Ala Val Thr Gly Glu Phe Thr Gly Ile Pro Glu
                85                  90                  95

Gln Trp Ala Arg Leu Leu Gln Thr Ser Asn Ile Thr Lys Leu Glu Gln
                100                 105                 110

Lys Lys Asn Pro Gln Ala Val Leu Asp Val Leu Lys Phe Tyr Asp Ser
        115                 120                 125

Lys Glu Thr Val Asn Asn Gln Lys Tyr Met Ser Phe Thr Ser Gly Asp
        130                 135                 140

Lys Ser Ala His Gly Tyr Ile Ala Ala His Pro Ser Ser Thr Lys Thr
145                 150                 155                 160

Ala Ser Glu Pro Pro Leu Ala Pro Pro Val Ser Glu Glu Asp Glu
                165                 170                 175

Glu Glu Glu Glu Glu Glu Asp Glu Asn Glu Pro Pro Val Ile Ala
                180                 185                 190

Pro Arg Pro Glu His Thr Lys Ser Ile Tyr Thr Arg Ser Val Val Glu
        195                 200                 205

Ser Ile Ala Ser Pro Ala Val Pro Asn Lys Glu Val Thr Pro Pro Ser
        210                 215                 220
```

```
Ala Glu Asn Ala Asn Ser Ser Thr Leu Tyr Arg Asn Thr Asp Arg Gln
225                 230                 235                 240

Arg Lys Lys Ser Lys Met Thr Asp Glu Glu Ile Leu Glu Lys Leu Arg
                245                 250                 255

Ser Ile Val Ser Val Gly Asp Pro Lys Lys Tyr Thr Arg Phe Glu
            260                 265                 270

Lys Ile Gly Gln Gly Ala Ser Gly Thr Val Tyr Thr Ala Leu Asp Ile
        275                 280                 285

Ala Thr Gly Gln Glu Val Ala Ile Lys Gln Met Asn Leu Gln Gln Gln
290                 295                 300

Pro Lys Lys Glu Leu Ile Ile Asn Glu Ile Leu Val Met Arg Glu Asn
305                 310                 315                 320

Lys Asn Pro Asn Ile Val Asn Tyr Leu Asp Ser Tyr Leu Val Gly Asp
                325                 330                 335

Glu Leu Trp Val Val Met Glu Tyr Leu Ala Gly Gly Ser Leu Thr Asp
            340                 345                 350

Val Val Thr Glu Thr Cys Met Asp Glu Gly Gln Ile Ala Ala Val Cys
        355                 360                 365

Arg Glu Cys Leu Gln Ala Leu Asp Phe Leu His Ser Asn Gln Val Ile
370                 375                 380

His Arg Asp Ile Lys Ser Asp Asn Ile Leu Leu Gly Met Asp Gly Ser
385                 390                 395                 400

Val Lys Leu Thr Asp Phe Gly Phe Cys Ala Gln Ile Thr Pro Glu Gln
                405                 410                 415

Ser Lys Arg Ser Thr Met Val Gly Thr Pro Tyr Trp Met Ala Pro Glu
            420                 425                 430

Val Val Thr Arg Lys Ala Tyr Gly Pro Lys Val Asp Ile Trp Ser Leu
        435                 440                 445

Gly Ile Met Ala Ile Glu Met Val Glu Gly Glu Pro Pro Tyr Leu Asn
450                 455                 460

Glu Asn Pro Leu Arg Ala Leu Tyr Leu Ile Ala Thr Asn Gly Thr Pro
465                 470                 475                 480

Glu Leu Gln Asn Pro Glu Arg Leu Ser Ala Val Phe Arg Asp Phe Leu
                485                 490                 495

Asn Arg Cys Leu Glu Met Asp Val Asp Arg Arg Gly Ser Ala Lys Glu
            500                 505                 510

Leu Leu Gln His Pro Phe Leu Lys Leu Ala Lys Pro Leu Ser Ser Leu
        515                 520                 525

Thr Pro Leu Ile Ile Ala Ala Lys Glu Ala Ile Lys Asn Ser Ser Arg
530                 535                 540

<210> SEQ ID NO 5
<211> LENGTH: 591
<212> TYPE: PRT
<213> ORGANISM: Homo sapiens

<400> SEQUENCE: 5

Met Phe Gly Lys Arg Lys Lys Arg Val Glu Ile Ser Ala Pro Ser Asn
1               5                   10                  15

Phe Glu His Arg Val His Thr Gly Phe Asp Gln His Glu Gln Lys Phe
                20                  25                  30

Thr Gly Leu Pro Arg Gln Trp Gln Ser Leu Ile Glu Glu Ser Ala Arg
            35                  40                  45

Arg Pro Lys Pro Leu Val Asp Pro Ala Cys Ile Thr Ser Ile Gln Pro
        50                  55                  60
```

```
Gly Ala Pro Lys Thr Ile Val Arg Gly Ser Lys Gly Ala Lys Asp Gly
 65                  70                  75                  80

Ala Leu Thr Leu Leu Leu Asp Glu Phe Glu Asn Met Ser Val Thr Arg
                 85                  90                  95

Ser Asn Ser Leu Arg Arg Asp Ser Pro Pro Pro Ala Arg Ala Arg
                100                 105                 110

Gln Glu Asn Gly Met Pro Glu Glu Pro Ala Thr Thr Ala Arg Gly Gly
                115                 120                 125

Pro Gly Lys Ala Gly Ser Arg Gly Arg Phe Ala Gly His Ser Glu Ala
                130                 135                 140

Gly Gly Ser Gly Asp Arg Arg Ala Gly Pro Glu Lys Arg Pro
145                 150                 155                 160

Lys Ser Ser Arg Glu Gly Ser Gly Gly Pro Gln Glu Ser Ser Arg Asp
                165                 170                 175

Lys Arg Pro Leu Ser Gly Pro Asp Val Gly Thr Pro Gln Pro Ala Gly
                180                 185                 190

Leu Ala Ser Gly Ala Lys Leu Ala Ala Gly Arg Pro Phe Asn Thr Tyr
                195                 200                 205

Pro Arg Ala Asp Thr Asp His Pro Ser Arg Gly Ala Gln Gly Glu Pro
                210                 215                 220

His Asp Val Ala Pro Asn Gly Pro Ser Ala Gly Gly Leu Ala Ile Pro
225                 230                 235                 240

Gln Ser Ser Ser Ser Ser Arg Pro Pro Thr Arg Ala Arg Gly Ala
                245                 250                 255

Pro Ser Pro Gly Val Leu Gly Pro His Ala Ser Glu Pro Gln Leu Ala
                260                 265                 270

Pro Pro Ala Cys Thr Pro Ala Ala Pro Ala Val Pro Gly Pro Pro Gly
                275                 280                 285

Pro Arg Ser Pro Gln Arg Glu Pro Gln Arg Val Ser His Glu Gln Phe
                290                 295                 300

Arg Ala Ala Leu Gln Leu Val Val Asp Pro Gly Asp Pro Arg Ser Tyr
305                 310                 315                 320

Leu Asp Asn Phe Ile Lys Ile Gly Glu Gly Ser Thr Gly Ile Val Cys
                325                 330                 335

Ile Ala Thr Val Arg Ser Ser Gly Lys Leu Val Ala Val Lys Lys Met
                340                 345                 350

Asp Leu Arg Lys Gln Gln Arg Arg Glu Leu Leu Phe Asn Glu Val Val
                355                 360                 365

Ile Met Arg Asp Tyr Gln His Glu Asn Val Val Glu Met Tyr Asn Ser
                370                 375                 380

Tyr Leu Val Gly Asp Glu Leu Trp Val Val Met Glu Phe Leu Glu Gly
385                 390                 395                 400

Gly Ala Leu Thr Asp Ile Val Thr His Thr Arg Met Asn Glu Glu Gln
                405                 410                 415

Ile Ala Ala Val Cys Leu Ala Val Leu Gln Ala Leu Ser Val Leu His
                420                 425                 430

Ala Gln Gly Val Ile His Arg Asp Ile Lys Ser Asp Ser Ile Leu Leu
                435                 440                 445

Thr His Asp Gly Arg Val Lys Leu Ser Asp Phe Gly Phe Cys Ala Gln
                450                 455                 460

Val Ser Lys Glu Val Pro Arg Arg Lys Ser Leu Val Gly Thr Pro Tyr
465                 470                 475                 480
```

```
Trp Met Ala Pro Glu Leu Ile Ser Arg Leu Pro Tyr Gly Pro Glu Val
                485                 490                 495

Asp Ile Trp Ser Leu Gly Ile Met Val Ile Glu Met Val Asp Gly Glu
            500                 505                 510

Pro Pro Tyr Phe Asn Glu Pro Pro Leu Lys Ala Met Lys Met Ile Arg
        515                 520                 525

Asp Asn Leu Pro Pro Arg Leu Lys Asn Leu His Lys Val Ser Pro Ser
    530                 535                 540

Leu Lys Gly Phe Leu Asp Arg Leu Leu Val Arg Asp Pro Ala Gln Arg
545                 550                 555                 560

Ala Thr Ala Ala Glu Leu Leu Lys His Pro Phe Leu Ala Lys Ala Gly
                565                 570                 575

Pro Pro Ala Ser Ile Val Pro Leu Met Arg Gln Asn Arg Thr Arg
            580                 585                 590
```

<210> SEQ ID NO 6
<211> LENGTH: 67
<212> TYPE: PRT
<213> ORGANISM: Homo sapiens

<400> SEQUENCE: 6

```
His Thr Ile His Val Gly Phe Asp Ala Val Thr Gly Glu Phe Thr Gly
1               5                   10                  15

Met Pro Glu Gln Trp Ala Arg Leu Leu Gln Thr Ser Asn Ile Thr Lys
            20                  25                  30

Ser Glu Gln Lys Lys Asn Pro Gln Ala Val Leu Asp Val Leu Glu Phe
        35                  40                  45

Tyr Asn Ser Lys Lys Thr Ser Asn Ser Gln Lys Tyr Met Ser Phe Thr
    50                  55                  60

Asp Lys Ser
65
```

<210> SEQ ID NO 7
<211> LENGTH: 13
<212> TYPE: PRT
<213> ORGANISM: Homo sapiens

<400> SEQUENCE: 7

```
Lys Pro Pro Ala Pro Pro Met Arg Asn Thr Ser Thr Met
1               5                   10
```

<210> SEQ ID NO 8
<211> LENGTH: 25
<212> TYPE: PRT
<213> ORGANISM: Artificial sequence
<220> FEATURE:
<223> OTHER INFORMATION: amino acid sequence of a synthetic peptide
      containing the PAK1 proline-rich sequence fused to the polybasic
      sequence from the HIV tat protein

<400> SEQUENCE: 8

```
Tyr Gly Arg Lys Lys Arg Arg Gln Arg Arg Gly Lys Pro Pro Ala
1               5                   10                  15

Pro Pro Met Arg Asn Thr Ser Thr Met
            20                  25
```

<210> SEQ ID NO 9
<211> LENGTH: 20
<212> TYPE: DNA
<213> ORGANISM: artificial sequence
<220> FEATURE:

```
-continued

<223> OTHER INFORMATION: first PCR primer for the targeting of conserved
      sequences between human and mouse PAK1 cDNAs

<400> SEQUENCE: 9
tggctggagg ctccttgaca                                                      20

<210> SEQ ID NO 10
<211> LENGTH: 22
<212> TYPE: DNA
<213> ORGANISM: artificial sequence
<220> FEATURE:
<223> OTHER INFORMATION: second PCR primer for the targeting of
      conserved sequences between human and mouse PAK1 cDNAs

<400> SEQUENCE: 10
gagggcttgg caatcttcag ga                                                   22

<210> SEQ ID NO 11
<211> LENGTH: 61
<212> TYPE: DNA
<213> ORGANISM: artificial sequence
<220> FEATURE:
<223> OTHER INFORMATION: first PCR primer for the amplification of the
      PAK1-ID

<400> SEQUENCE: 11
atcgccacca tgtaccctta tgatgtgcca gattatgccc acacaattca tgtcggtttt         60
g                                                                         61

<210> SEQ ID NO 12
<211> LENGTH: 28
<212> TYPE: DNA
<213> ORGANISM: artificial sequence
<220> FEATURE:
<223> OTHER INFORMATION: second PCR primer for the amplification of the
      PAK1-ID

<400> SEQUENCE: 12
atcttatgac ttatctgtaa agctcatg                                             28
```